(12) United States Patent
Poirier

(10) Patent No.: US 11,786,352 B2
(45) Date of Patent: Oct. 17, 2023

(54) DEVICE FOR ARTIFICIAL INSEMINATION, GYNAECOLOGICAL EXAMINATION OF THE VAGINA AND THE CERVIX, AND TO ASSIST WITH UTERINE TREATMENTS AND SAMPLE COLLECTION IN LIVESTOCK

(71) Applicant: INOVET TECHNOLOGY, Martigne-Ferchaud (FR)

(72) Inventor: Antoine Poirier, Martigne-Ferchaud (FR)

(73) Assignee: INOVET TECHNOLOGY, Martigne-Ferchaud (FR)

( * ) Notice: Subject to any disclaimer, the term of this patent is extended or adjusted under 35 U.S.C. 154(b) by 624 days.

(21) Appl. No.: 16/772,461

(22) PCT Filed: Dec. 13, 2018

(86) PCT No.: PCT/EP2018/084831
§ 371 (c)(1),
(2) Date: Jun. 12, 2020

(87) PCT Pub. No.: WO2019/115726
PCT Pub. Date: Jun. 20, 2019

(65) Prior Publication Data
US 2021/0093432 A1  Apr. 1, 2021

(30) Foreign Application Priority Data

Dec. 13, 2017 (FR) ...................... 1762044

(51) Int. Cl.
*A61D 19/02* (2006.01)
*A61B 1/00* (2006.01)
(Continued)

(52) U.S. Cl.
CPC ........ *A61D 19/027* (2013.01); *A61B 1/00016* (2013.01); *A61B 1/05* (2013.01); *A61B 1/0676* (2013.01); *A61B 1/303* (2013.01)

(58) Field of Classification Search
CPC .... A61D 19/027; A61B 1/0016; A61B 1/303; A61B 1/0676; A61B 1/05
See application file for complete search history.

(56) References Cited

U.S. PATENT DOCUMENTS

| 2005/0288606 | A1  | 12/2005 | Alter |
| 2006/0217590 | A1* | 9/2006  | Tack ................... A61D 19/027 600/35 |
| 2009/0171159 | A1* | 7/2009  | Jorgensen .......... A61B 18/1492 600/139 |
| 2013/0131667 | A1* | 5/2013  | Jenson ............... A61B 18/1492 606/41 |

(Continued)

FOREIGN PATENT DOCUMENTS

| CA | 3012955 A1    | 8/2017 |
| WO | 2017129929 A1 | 8/2017 |

OTHER PUBLICATIONS

International Search Report dated Mar. 20, 2019 for corresponding International Application No. PCT/EP2018/084831, filed Dec. 13, 2018.

(Continued)

*Primary Examiner* — Christine H Matthews
*Assistant Examiner* — Joshua Daryl D Lannu
(74) *Attorney, Agent, or Firm* — David D. Brush; Westman, Champlin & Koehler, P.A.

(57) ABSTRACT

A device for artificial insemination, gynaecological examination of the vagina and the cervix, intra-uterine treatments and uterine sample collection in livestock. The device includes: a guiding sleeve having a proximal end for being positioned in the reproductive system of the animal and a distal end for being handled by the user; a gynaecological instrument, such as an insemination gun, an insemination or treatment catheter, or a sample-collection swab, slidingly housed in the guiding sleeve, the instrument being capable (Continued)

of being operated by the user at the rear end thereof, located on the side of the distal end of the guiding sleeve, in order for the front end thereof to lead through an opening located at the proximal end of the guiding sleeve so as to allow the insemination, treatment or sample collection. The guiding sleeve has a blocking element for blocking the sliding of the instrument inside the guiding sleeve.

16 Claims, 6 Drawing Sheets

(51) Int. Cl.
  *A61B 1/05* (2006.01)
  *A61B 1/06* (2006.01)
  *A61B 1/303* (2006.01)

(56) References Cited

U.S. PATENT DOCUMENTS

2017/0084027 A1\* 3/2017 Mintz ............... A61B 34/20
2019/0038115 A1   2/2019 Decherf et al.

OTHER PUBLICATIONS

Written Opinion of the International Searching Authority dated Mar. 20, 2019 for corresponding International Application No. PCT/EP2018/084831, filed Dec. 13, 2018.

International Preliminary Report on Patentability and English translation of the International Written Opinion dated Mar. 28, 2019 for corresponding International Application No. PCT/EP2018/084831, filed Dec. 13, 2018.

European Notification under Article 94(3) EPC dated Jul. 5, 2023 for corresponding European Application No. 18826246.3.

\* cited by examiner

DEVICE FOR ARTIFICIAL INSEMINATION, GYNAECOLOGICAL EXAMINATION OF THE VAGINA AND THE CERVIX, AND TO ASSIST WITH UTERINE TREATMENTS AND SAMPLE COLLECTION IN LIVESTOCK

CROSS-REFERENCE TO RELATED APPLICATIONS

This Application is a Section 371 National Stage Application of International Application No. PCT/EP2018/084831, filed Dec. 13, 2017, which is incorporated by reference in its entirety and published as WO 2019/115726 A1 on Jun. 20, 2019, not in English.

1 FIELD OF INVENTION

This invention relates to the design and construction of gynaecological devices particularly, but not exclusively, intended for the artificial insemination, examination of the vagina and cervix, or veterinary treatment of livestock such as cows or mares.

2 STATE OF THE ART

Artificial insemination of livestock, such as cows or mares, is widely used for reproduction.

This biotechnology allows the rapid and widespread diffusion of male reproductive genes in a manner known per se and in optimal sanitary conditions.

Artificial insemination thus helps improve animal performance and promote the exchange of genetic material.

At present there are a number of artificial insemination techniques, one of which entails the use of an insemination device that is inserted into the vagina of the animal by an operator so as to reach the cervix, traverse it, and inject a semen dose contained in a straw into the uterus.

In general, an insemination device with semen contained in a straw comprises a rigid tubular body, forming a sheath or sleeve, inside of which is a sliding rod.

The front end of the insemination device, which receives the straw filled with semen, is designed for insertion into the cervix and then uterus, aided by the operator inserting a hand and arm into the rectum of the animal in order to hold and manoeuvre the cervix through the rectal wall, so as to facilitate the insertion of the insemination device into the cervix so that the insemination device passes the cervix and its front end reaches the uterine corpus. The rear end of the insemination device is designed to be used in the other hand of the operator to slide the rod and eject the semen once the device is in place in the uterus of the animal.

This solution, however, has its drawbacks.

One disadvantage lies in the fact that, when the insemination device is inserted into the animal, its front end is no longer visible to the operator, who must therefore work by sense of touch alone. This requires a degree of technical skill that can only be achieved after a lengthy training process and that can, in unskilled hands, result in injury to the animal.

In some cases, the vagina of the animal has multiple folds that obstruct passage of the insemination device.

In addition, it can sometimes be difficult to locate the entry point to the cervix, which itself may have several annular rings that can be narrow and difficult to traverse.

The insertion of the insemination device can distress the animal and cause the vaginal and cervical muscles to contract, temporarily preventing the device from moving further.

Another disadvantage lies in the fact that "blindly" inserting the insemination device into the reproductive tract of the animal might cause injury if its pointed end scrapes against the vaginal mucosa.

This may also occur if the animal moves unexpectedly during the procedure.

Another disadvantage lies in the fact that the operator must insert a hand and arm into the rectum of the animal, in order to hold and manoeuvre the cervix through the rectal wall so that the insemination device can be inserted from the cervix to the uterine corpus, which is uncomfortable for the animal, particularly since the operation can last a long time.

Another disadvantage lies in the fact that the operator must insert a hand and arm into the rectum of the animal, in order to hold and manoeuvre the cervix through the rectal wall so that the insemination device can be inserted from the cervix to the uterine corpus, which is uncomfortable for the operator, particularly since the operation can last a long time, and if repeated several times a day can result in chronic musculoskeletal pain for the operator.

Insemination devices that comprise a vision system on a remote display, making it possible to locate the cervix, have partially resolved the problems inherent to the state of art. However, due to their larger diameter, they are uncomfortable for the animal and lack the manoeuvrability to traverse the cervix of some animals.

3 SUMMARY OF INVENTION

The purpose of this invention is to solve some or all of the problems with the state of art.

More precisely, the objective of the invention is to propose a technique that is simpler to use, less stressful for the animal, simple in design, easy to implement and inexpensive to produce.

Another objective of the invention is to offer a technique that minimises the time the farmer must spend with each animal.

The third objective of this invention is to offer a technique that facilitates the artificial insemination, examination of the reproductive system, or veterinary treatment of livestock.

To this end, the invention relates to a device for artificial insemination, gynaecological examination of the vagina and cervix, intrauterine treatments and uterine sample collection in livestock, comprising:

- a guiding sleeve with a proximal end intended to be positioned in the reproductive system of the animal and a distal end intended to be handled by the user;
- a gynaecological instrument, such as an insemination gun, insemination or treatment catheter, or sampling swab, that slides within the guiding sleeve and can be operated by the user at its rear end, located beside the distal end of the guiding sleeve, so that the front end passes through an opening located at the proximal end of the guiding sleeve for the purposes of insemination, treatment or sample collection.

According to the invention, the guiding sleeve is equipped with locking means for blocking the sliding movement of the instrument inside the guiding sleeve.

This solution enables improved control/handling, particularly of the instrument sliding inside the sleeve during an insemination procedure, for example. Thus, when the user holds the device in one hand, he/she is able to lock the insemination gun at any time as its front end progresses past the cervix into the uterus, and thus prevent any unintentional back movement of the insemination gun into the guiding sleeve. This solution also enables the insemination gun to be secured within the guiding sleeve, so that the front end of the insemination gun gradually progresses through the cervix as the entire device is advanced within the reproductive tract of the animal.

According to one specific aspect of the invention, the locking means are located on the distal end of the guiding sleeve.

This location of the locking means allows the user to hold the guiding sleeve and operate the locking means with the same hand. The operator can thus use his/her other hand to manoeuvre the instrument.

One advantage is that the locking means comprise at least one mobile pad that can be set to one of two positions: a locked position wherein at the least said pad is in contact with the instrument and prevents it from moving, and a retracted position wherein at the least said pad is not in contact with the instrument and permits it to slide.

According to a particular application, the locking means comprise a single friction pad able to exert friction force against the instrument.

Such locking means have the benefit of being simple and inexpensive to manufacture.

According to another particular application, the locking means comprise at least two pads in a jaw configuration that are able to exert a pinch force around the instrument.

This locking configuration improves distribution of the friction force on the peripheral surface of the instrument, and thus minimises the risk of damage to the instrument.

These locking means shall preferably comprise a manual pivoting tab to operate said means.

Thus, the instrument may be prevented from sliding within the guiding sleeve by simply switching the tab with the thumb of the operator. This solution is reliable and ergonomic.

A further advantage is the fact that the guiding sleeve comprises a gripping assembly located near the locking means.

As such, it is possible to activate the locking means and insert the device into the animal using the same hand. The gripping assembly also allows the operator to easily manoeuvre the insemination device with great precision using his/her other hand.

The gripping assembly will preferably comprise a ring located underneath the guiding sleeve, designed for the index finger of the operator.

The configuration of this gripping assembly enables the user to hold and operate the device by pinching only. The user can thus manoeuvre the device with ease and precision, and can avoid roughly handling and/or injuring the animal. This configuration also allows the user to insert the device deeper, or even entirely, into the reproductive tract of the animal.

According to a particular application, the gripping assembly also comprises a concave surface on the top of the guiding sleeve, intended to receive the thumb of the user.

A further advantage is that the proximal end of the guiding sleeve comprises a camera.

Said camera aids the operator by allowing him/her to easily guide the instrument and monitor the progress of the operation being performed, such as insemination. The specific location of the camera ensures a greater freedom of movement for the guiding sleeve. The operator can therefore easily position the front end of the instrument near the target area.

According to a particular application, the camera is integrated inside of the guiding sleeve.

This location of the camera facilitates the insertion of the artificial insemination device inside the reproductive tract of the animal. This improves the comfort of the animal during use of the device. For example, placing the camera inside the sleeve minimises the risks of the device being obstructed by folds in the reproductive tract of the animal.

A further advantage is that the device comprises transmission means for transmitting the images captured by the camera to a remote display screen, whereby the transmission means are integrated inside the distal end of the guiding sleeve.

This configuration enables optimal transfer of captured images to the remote display (such as a smartphone), even when the device is inserted deep or entirely within the reproductive tract of the animal.

According to a specific aspect of the invention, the diameter of the guiding sleeve is between 6 mm and 25 mm.

This reduced diameter of the guiding sleeve offers greater freedom of movement of the device when inside the body of the animal. The operator can therefore easily position the front end of the instrument near the target area.

According to a preferential aspect of the invention, the guiding sleeve comprises two parts that are secured together in a removable manner via a complementary interlocking means.

Preferably, the complementary interlocking means comprises sealing means at the junction between the two parts.

According to a specific aspect, the device comprises a sanitary sheath inside the guiding sleeve, with said guiding sleeve also comprising retaining means for the sanitary sheath inside said sleeve.

4 LIST OF FIGURES

Other features and advantages of the invention will become more apparent upon reading the following description of embodiments, hereby given to serve as illustrative and non-restrictive examples, and the attached drawings, which include:

5 DETAILED DESCRIPTION OF THE INVENTION

This section describes the invention device when it is used for the artificial insemination of livestock, with the gynaecological instrument taking the form of an insemination gun.

In other applications, the invention device is used for the uterine treatment of livestock, with the gynaecological instrument in this specific case taking the form of a catheter that can be used for the delivery of treatment products, such as those used to combat infection or sterility.

In other applications, the invention device is used to collect uterine samples from livestock, with the gynaecological instrument in this specific case taking the form of a swab.

In other applications, the invention device is used for the vaginal and cervical examination of livestock, which in this specific case is used without a gynaecological instrument.

5.1 Preferred Embodiment

FIGS. 1 to 9 illustrate a device for the artificial insemination and vaginal and uterine examination, treatment and sample collection for livestock, according to the preferred embodiment of the invention.

Figure 1:
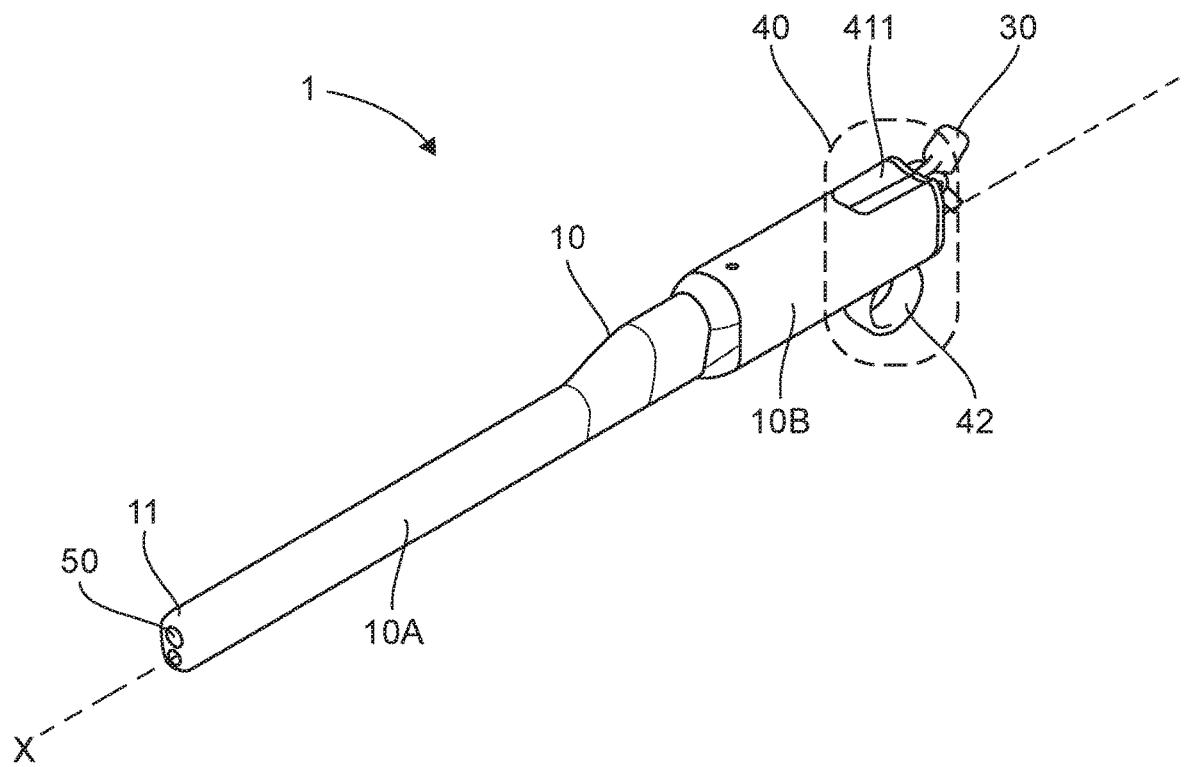
FIG. 1 is a perspective view of a device for the artificial insemination and vaginal and uterine observations and sample collection for livestock, according to the preferred embodiment of the invention.
Figure 2:
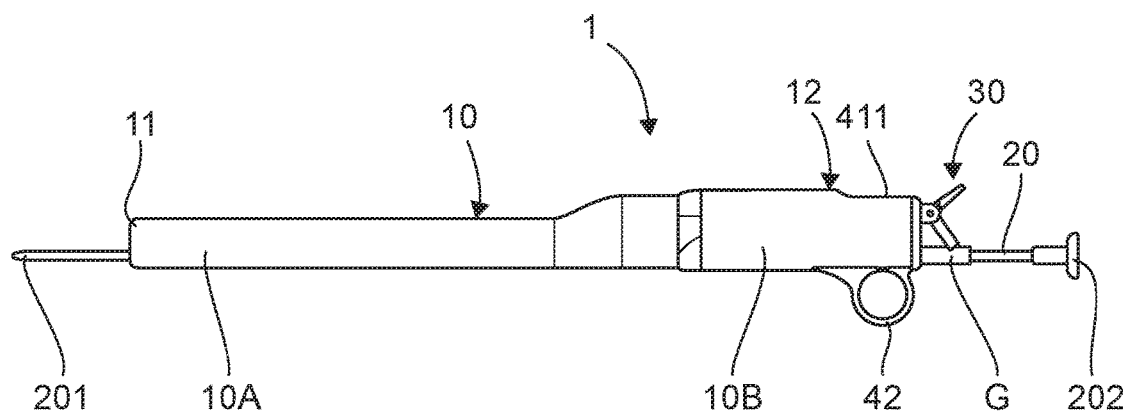
FIG. 2 is a side view of the device shown in FIG. 1.

The device 1 comprises, as illustrate in FIGS. 1 and 2, a guiding sleeve 10 having a proximal end 11, intended for insertion in the vagina of the animal, and a distal end 12, intended to be handled by a user during an insemination procedure.

Furthermore, the device 1 comprises an insemination gun 20 with one end, called front end 201, intended to be positioned in the uterus of the animal, and a second end, called rear end 202, intended to be used by the operator to inject the contents of a semen straw into the uterus of the animal.

The insemination gun 20 is inserted in a tubular sanitary sheath G made from semi-rigid plastic, to protect the interior of the guiding sleeve against the bodily fluids of the animal and thus prevent bacterial contamination. The sanitary sheath G is designed to be crimped inside the guiding sleeve 10 of the device 1. A tapered cone inside the guiding sleeve 10 crimps the sanitary sheath G to the inside of the guiding sleeve 10.

The insemination gun 20 is housed in a sliding manner inside the sanitary sheath G, which itself is secured in a fixed position inside the guiding sleeve 10 and positioned so that the read end of the insemination gun 20 is located alongside the distal end of the guiding sleeve 10 and that the front end is located alongside the proximal end of the guiding sleeve 10.

The proximal end 11 of the guiding sleeve 10 has an opening through which the front end 201 of the insemination gun 20 can pass.

According to the invention, the device 1 for the artificial insemination of livestock comprises locking means 30 for blocking the sliding of the insemination gun 20 inside the guiding sleeve 10 (through the sanitary sheath G). Specifically, the locking means 30 are located at the distal end 12 of the guiding sleeve 10.

Such locking means 30 make it possible to control the progression of the insemination gun 20 within the guiding sleeve 10 with precision and ease during insemination procedures, so that the front end 201 of the insemination gun 20 gradually moves past the cervix. It also prevents the accidental withdrawal of the insemination gun 20 back into the guiding sleeve 10, particularly when the operator is holding the device 1 with a single hand.

Furthermore, such locking means 30 connect the insemination gun 20 to the guiding sleeve 10 during an insemination procedure, so that the front end 201 of the insemination gun 20 gradually moves past the cervix as the entire device 1 is moved through the reproductive tract, particularly when the operator is holding the device 1 with a single hand.

Such locking means 30 also make it possible to control the progression of the insemination gun 20 within the guiding sleeve 10 during insemination procedures, in order to prevent the insemination gun 20 from penetrating too deep into the reproductive tract of the animal.

Furthermore, such locking means retains the insemination gun 20 in the guiding sleeve 10 when the operator transports the device 1.

Figure 7:
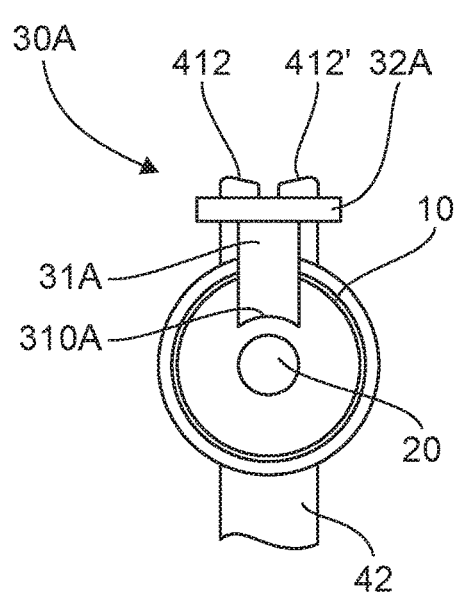
FIG. 7 is a schematic view showing a first example of the locking means implemented in a device according to the invention.
Figure 8:
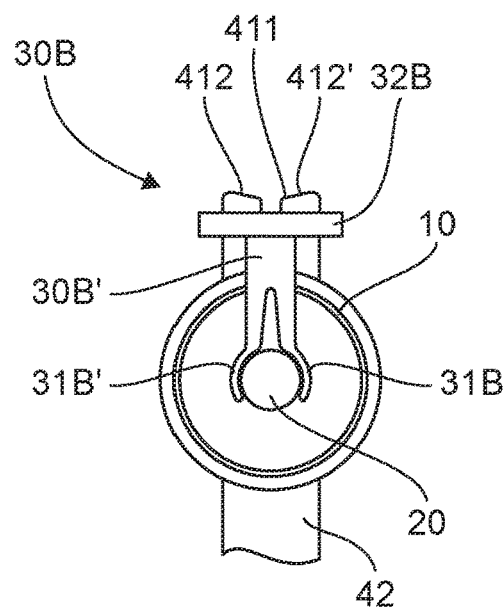
FIG. 8 is a schematic view showing a second example of the locking means implemented in a device according to the invention.

FIGS. 7 and 8 are schematic views showing two examples of locking means implemented in the invention device.

FIG. 7 illustrates one example of locking means 30A for blocking the sliding of the insemination gun 20 inside the guiding sleeve 10.

In this example, the locking means 30A have a single friction pad 31A that is mobile and able to exert a friction force against the body of the insemination gun 20 either directly or via the sanitary sheath G.

More precisely, the mobile pad 31A is connected to the manual actuating means 32A to lock or unlock the sliding action of the insemination gun 20 in the guiding sleeve 10.

As such, the locking means 30A can assume two positions: a locking position in which the pad 31A is in contact with the insemination gun 20 either directly or via the sanitary sheath G, and a retracted position in which the pad 31A is located away from the insemination gun 20 so that said insemination gun 20 is able to move in a sliding motion.

The specific location of this locking means 30A, at the distal end 12 of the guiding sleeve 10, allows the user to handle the guiding sleeve 10 and insemination gun 20 with a single hand.

The user can thus regulate the movement of the insemination gun 20 in the guiding sleeve 10 with ease and precision, and lock the insemination gun 20 in position inside the guiding sleeve 10.

As illustrated, the mobile pad 31A, which takes the form of a rectangular element, comprises one end connected to an actuating tab 32A and another end, opposite the first, that is free and has a concave surface 310A. The pad 31A and actuating tab 32A substantially form an angle of 90°.

The tab 32A is mounted in a pivoting manner onto a bracket 41, which in turn is attached to the distal end 12 of the guiding sleeve 10.

To this end, the pivoting tab 32A comprises lateral pins (not shown) formed on each side of the latter that are housed in openings 410 built into the bracket 41. More specifically, the lateral lugs are positioned near the point where the tab 32A and pad 31A meet.

This pivoting configuration of the locking means 30A means that, when the user moves the tab 32A downwards, the mobile pad 31A comes into contact with the insemination gun locked position, and when the user moves the tab 32A upwards, the mobile pad 31A releases the insemination gun (retracted position).

This configuration also allows the user to operate the locking means 30A with a simple movement of the thumb.

In other words, when the user activates the locking means 30A to stop the insemination gun 20 from sliding, the user pivots the tab 32A downwards with a push of his/her thumb so that the pad 31A also pivots downwards and exerts sufficient pressure on the insemination gun 20 to immobilise it. When the insemination gun 20 is immobilised, the pad 31A is positioned as shown in FIG. 2.

FIG. 8 illustrates a second example of locking means 30B for blocking the sliding of the insemination gun 20 inside the guiding sleeve 10.

The example illustrated in FIG. 8 differs from the example illustrated in FIG. 7 solely in the structure of the mobile pad.

In this example, the locking means 30B comprises two mobile pads 31B, 31W able to exert a pinch force on the peripheral surface of the insemination gun 20 so as to prevent its movement.

As illustrated, the pads 31B, 31W are symmetrical and form a jaw-like configuration extending from a base 311B, which itself is integrated in the actuating tab 32B.

Thus, when the user activates the locking means 30B to stop the insemination gun 20 from sliding, the user pivots the tab 32B with his/her thumb so that the pads 31B, 31B' exert a sufficient pinch force on the peripheral surface of the insemination gun 20 to immobilise it.

The invention device 1 has particular applications in the artificial insemination, vaginal and cervical examination, and uterine treatment and sample collection of livestock, although it is not restricted to these applications.

One advantage is the guiding sleeve 10, as illustrated in FIGS. 1 to 6 and 9, comprises one sleeve part 10A that is joined to a second sleeve part 10B by removable fasteners. The first sleeve part 10A forms the front part of the sleeve 10, and the second sleeve part 10B forms the rear part of the sleeve 10. In other words, the proximal end 11 of the device 1 is located on the first sleeve part 10A, and the distal end 12 is located on the second sleeve part 10B.

Figure 3:
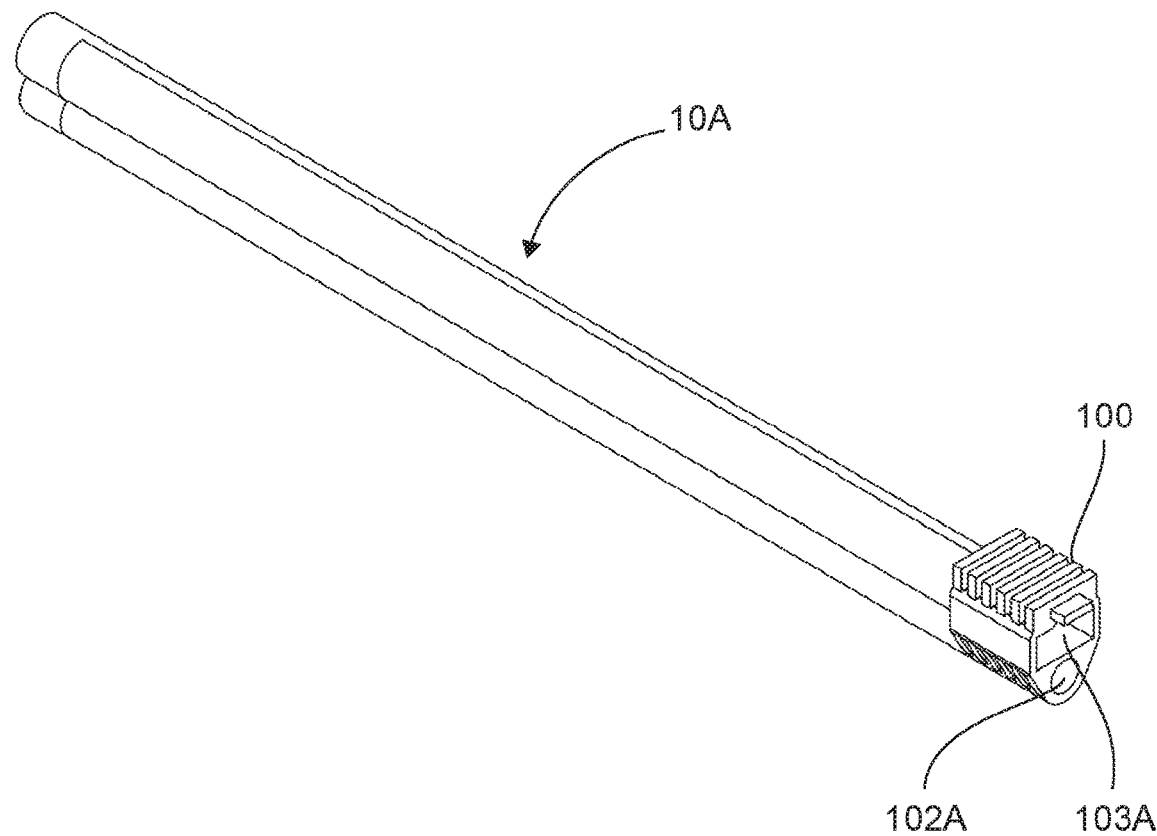
FIG. 3 is a perspective view of the first part of the guiding sleeve of the device shown in FIG. 1.
Figure 6:
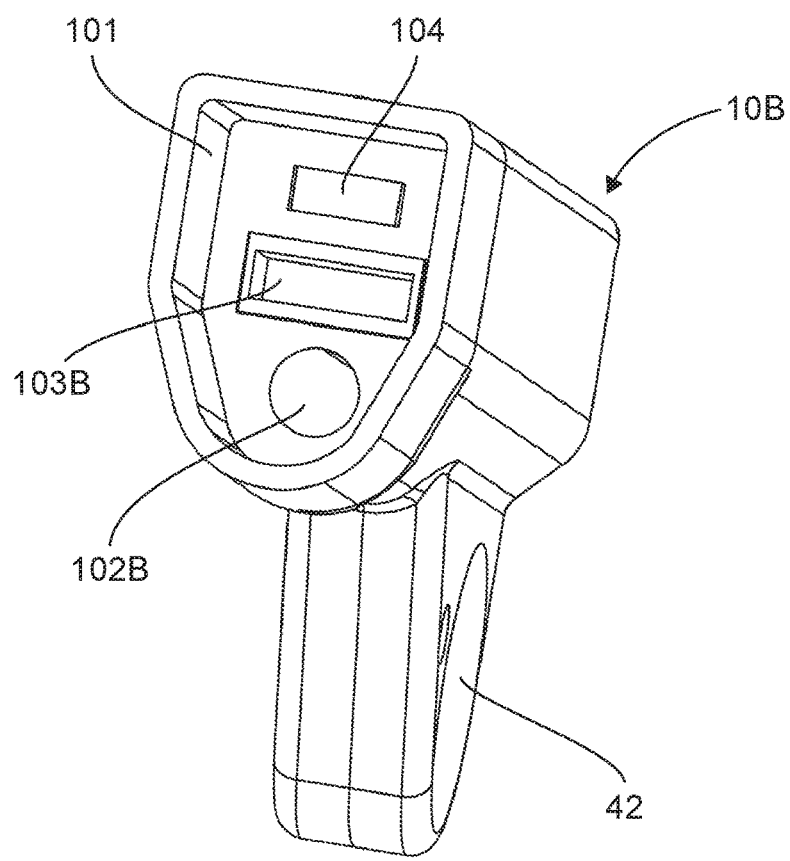
FIG. 6 is a perspective view of the second part of the guiding sleeve of the device shown in FIG. 1.

As illustrated in FIGS. 3 and 6, the first sleeve part 10A comprises one guide channel 102A, and the second sleeve part 10B comprises a second guide channel 102B to allow the sliding motion of the insemination gun 20.

Figure 9:
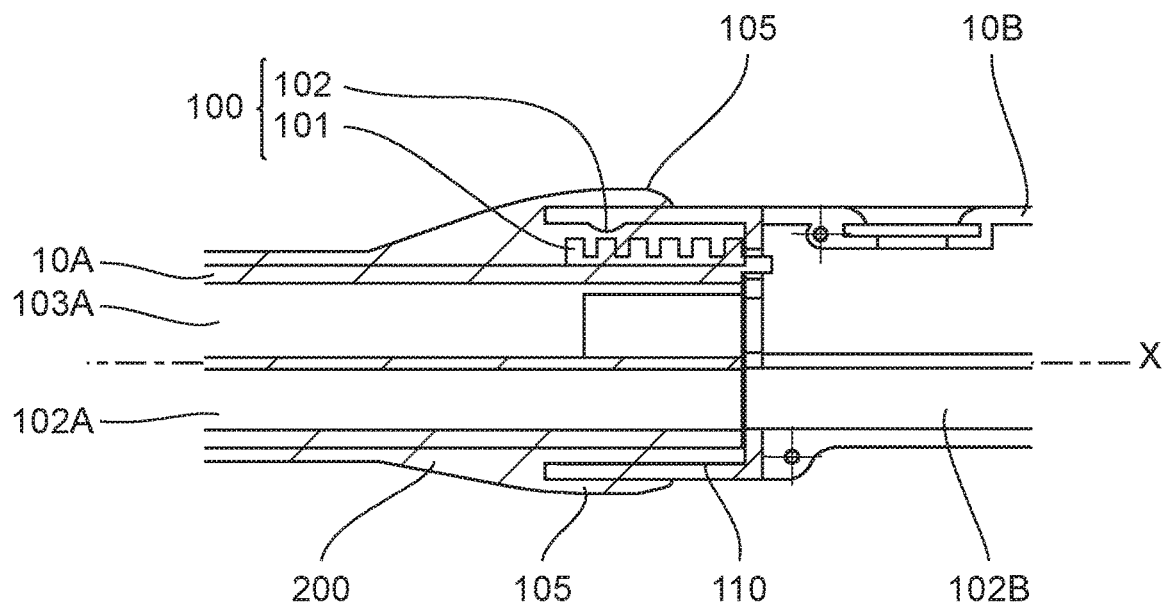
FIG. 9 is a longitudinal cross-section focused on the connection point of the two parts of the guiding sleeve of the device shown in FIG. 1.

The two guide channels 102A, 102B have the same diameter and are designed to align when the first and second sleeve parts 10A, 10B are assembled, as shown in FIG. 9.

Figure 4:
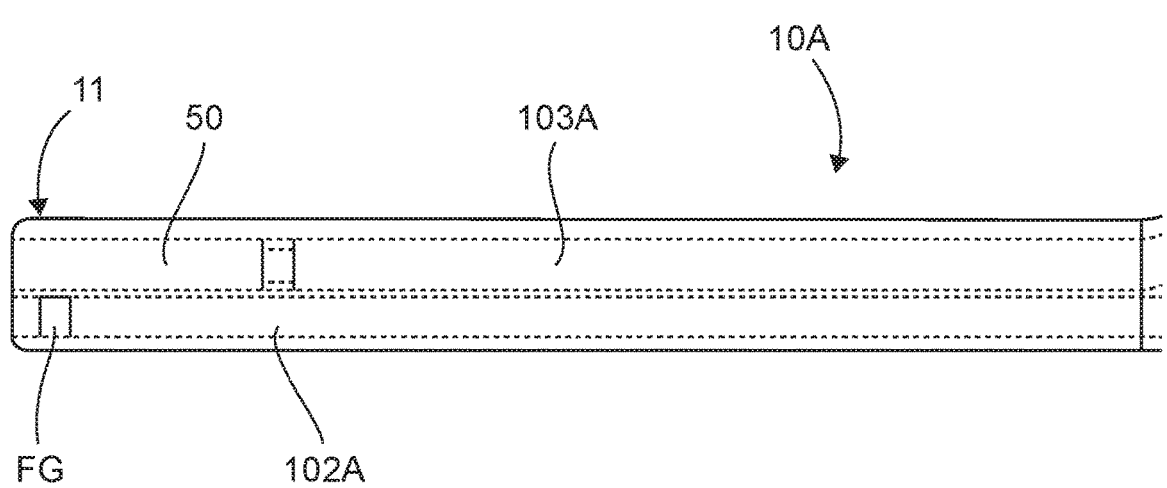
FIG. 4 is a partial and transparent view of the first part of the guiding sleeve shown in FIG. 3.

As illustrated in FIG. 4, the first sleeve part 10A comprises retaining means FG for the sanitary sheath G inside the first guide channel 102A.

More specifically, a portion of the inside surface of the first guide channel 102A is frustoconical in shape. This frustoconical surface comprises the retaining means FG for the sanitary sheath G. As such, when the user inserts the sanitary sheath G in the guide channel 102A, the frustoconical surface FG retains the sanitary sheath G by a crimping action.

When the first and second sleeve parts 10A, 10B are assembled, they form a single unit extending along a longitudinal x axis.

The reversible assembly of the first and second sleeve parts 10A, 10B is assured by complementary interlocking means.

As such, the two separate parts 10A, 10B of said guiding sleeve 10 are reversibly joined together by complementary interlocking means that comprise a joint seal between the two parts, as will be discussed later.

As illustrated in FIG. 9, the first sleeve part 10A comprises a removable fastener 100 designed for use in conjunction with the second removable fastener 110 on the second sleeve part 10B.

More specifically, the first removable fastener 100 comprises multiple notches 101 with a flexible internal element 102 spanning the edges of the distal end of the first sleeve part 10A.

The second removable fastener comprises a hollow 110 along the longitudinal x axis in the proximal end of the second sleeve part 10B.

The first removable fastener 100 is designed to slot into the second removable fastener 110. The compression of the flexible internal element 102 ensures a robust joint and internal sealing between the two parts comprising the sleeve.

Furthermore, the first sleeve part 10A comprises a flexible external element 105 designed to partially cover the external surface of the second sleeve part 10B when both sleeve parts 10A, 10B are assembled.

The flexible external element 105 improves the seal at the junction between the first and second sleeve parts 10A, 10B. The flexible external element 105 also improves the comfort of the animal when the device 1 is inserted into the reproductive tract.

Furthermore, the device 1 comprises a gripping assembly 40 allowing the user to easily manipulate the guiding sleeve 10 during insemination, for example.

The gripping assembly 40 is located at the distal end 12 of the guiding sleeve 10 so as to allow the user to rapidly activate the locking means 30 with a single hand.

Figure 5:
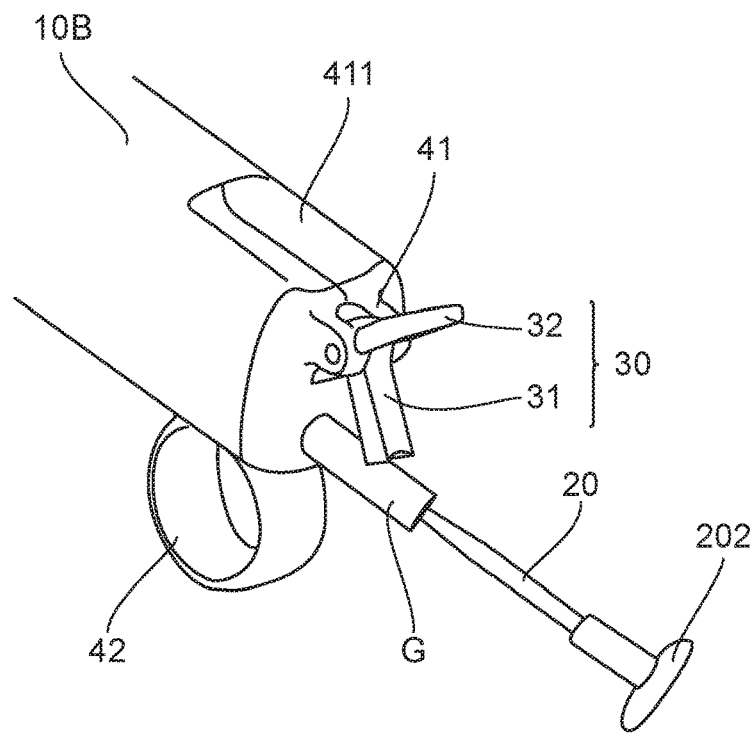
FIG. 5 is a perspective view focused on the distal end of the device shown in FIG. 1.

As illustrated in FIG. 1, and further visible in FIG. 5, the gripping assembly 40 comprises a ring 42 intended for the index finger of the hand of the user, and a concave surface 411 designed to receive the thumb of the same hand.

The concave surface 411 of an uppermost portion of the second sleeve part 10B is located near the tab 32.

This layout allows the user to place his/her thumb on the concave surface 411 when not operating the locking means 30.

The ring 42 is located underneath the guiding sleeve 10, opposite the concave surface 411. The opening of the ring 42 is oriented perpendicular to the longitudinal axis x of the device.

The configuration of this gripping assembly allows the user to hold and operate the device 1 by simply pinching with the thumb and index finger of the same hand.

This gripping assembly 40 allows the user to manipulate the insemination device 1 with ease, whether he/she is left-handed or right-handed.

The user can thus manoeuvre the device 1 with ease and precision, and can avoid roughly handling and/or injuring the animal. Furthermore, eliminating the handle allows the user to insert the device deeper, or even entirely, into the reproductive tract of the animal.

Note that the device could solely comprise a ring 42 located underneath the device, without implementing the concave surface on the top of the device.

In addition, the device 1 comprises a camera 50 that allows the user to see, on a remote monitor (not shown), the area of the reproductive tract of the animal where the proximal end 11 of the guiding sleeve 10 is currently located.

Thanks to this camera 50, the user can easily guide the device 1 inside the reproductive tract of the animal, move the guiding sleeve 10 and locate the entry to the cervix of the animal.

Once the entry to the cervix has been located, the camera 50 allows the operator to insert the front end 201 of the insemination gun 20 into the cervix, and to then pass through the cervix without a display until the front end 201 of the insemination gun 20 enters the uterus that will receive the straw filled with semen, and to complete the insemination procedure by injecting the semen inside the uterus.

The camera 50 allows the user to perform the insemination procedure with ease.

In addition, the images captured by the camera 50 are processed by an electronic unit (not shown) comprising:
an electrical power source, such as a battery or cell;
a microprocessor to process the captured images; and
the means to transmit the captured images to a remote monitor.

In this embodiment, the camera 50 is located at the proximal end 11 of the device 1, while the electronic unit is separate and located near the distal end 12. This configuration enables the transmission of captured images even when the device 1 is inserted deep in the reproductive system of the animal.

The device 1 also comprises an electrical conduit 103A for the electric cables that link the camera 50 to the electronic unit.

As illustrated in FIG. 1, and further visible in FIG. 4, the camera 50 is located in a housing at the proximal end 11 of the first sleeve part 10A.

This configuration facilitates insertion of the device 1 into the reproductive tract of the animal. This minimises the risk of the camera 50 being obstructed in the tight folds within the reproductive tract of the animal.

Furthermore, the electrical conduit 103A is also located inside the first sleeve part 10A. The electrical conduit 103A is separate from the guide channel 102A and extends above it.

As illustrated in FIG. 6, the second sleeve part 10B comprises a first electrical connector 103B that is linked to the electronic unit housed inside the second sleeve part 10B.

This first electrical connector 103B is designed to be removably connected to one or more electrical power and data transfer cables for the camera 50.

In addition, the second sleeve part 10B comprises a second electrical connector 104 designed to be removably connected to a charging cable for the electrical power supply.

The electrical connectors 103A and 104 are housed in the hollow 110 in order to simplify the electrical connection between the camera 50 and the electronic unit.

This configuration also protects the electrical connectors 103A and 104 from ambient moisture and fluids from the animal during use.

The device 1 can therefore be washed by water jet after the procedure, if necessary.

In this embodiment, the camera 50 is a digital camera that enables the user to monitor insertion of the device 1 into the reproductive tract of the animal in real time.

More specifically, the resolution of the camera is preferably 1280×720 pixels or 1920×1080 pixels, so that the entry to the cervix can be identified with precision.

In this embodiment, the camera 50 comprises light sources, chiefly LED, to illuminate the area of the reproductive system of the animal in front of the proximal end 11 of the guiding sleeve 10.

In this embodiment, the captured images are transmitted wirelessly via an antenna hidden inside the second sleeve part 10B. A variant of this is wired image transmission. To this end, the second sleeve part 10B comprises a specific connector for a communication cable linked to the remote monitor.

In this embodiment, the guiding sleeve 10 is made from a plastic material, to reduce the weight of the device 1 and facilitate handling.

Preferably, the guiding sleeve 10 is made by thermoforming.

In this embodiment, the first sleeve part 10A has an external diameter between 10 mm and 25 mm. More specifically, the first sleeve part 10A has a width of 14.5 mm and a height of 22 mm. The diameter, which is relatively small, facilitates insertion of the device 1 into the reproductive tract of the animal, passage past the occasionally tight folds in the vagina of the animal, and manoeuvrability of the device 1, all of which allow the operator to quickly locate and easily penetrate the entry to the cervix.

In this embodiment, the electrical connectors are USB (Universal Serial Bus) ports.

In this embodiment, the flexible internal and external elements 102, 201 are formed of a fixed single element 200 by overmoulding on the edge of the distal end of the first sleeve part 10A.

In this embodiment, the single element 200 is made from a flexible polymer material such as an elastomer, and particularly a medical-grade elastomer.

A variant of this is that the flexible polymer is placed across the entire external surface of the first sleeve part 10A, so as to facilitate insertion of the device 1 into the reproductive tract of the animal.

According to a particular approach, the device 1 has a single-use plastic insemination sheath (not shown) which caps the insemination gun 20 and is attached to it (it is part of and slides with the gun). This insemination sheath has a sanitary function, but also serves to protect the reproductive system against the tubular metal gun. It is also used for insemination (by emptying the straw). The insemination gun capped with an insemination sheath is capable of sliding within the sanitary sheath G.

A device for the artificial insemination, vaginal and cervical examination, and uterine treatments and sample collection of livestock according to the first embodiment of the invention has a number of advantages, namely:
a quick, easy and efficient method to lock/unlock the sliding action of the insemination instrument inside the guiding sleeve. The locking means also allow the insemination instrument to form an integral whole, so that it can progress along with the device to the final stage of semen injection. This locking means also prevents unintentional back movement of the insemination instrument during each stage of the procedure;
a small diameter that improves the manoeuvrability of the device, so that the user may locate the entry to the cervix of the animal more easily, insert the front end of the insemination gun 20 into the cervix more easily, and align the device 1 with the cervix of the animal to facilitate its passage. This small diameter also provides comfort of use to the operator as well as the animal for the duration of the procedure; and
a light weight, even when the insemination instrument is placed in the device, enabling easy handling by simply pinching the thumb and index finger, without the need for a handle along the guiding tube.

5.2 Second Embodiment

Figure 10:
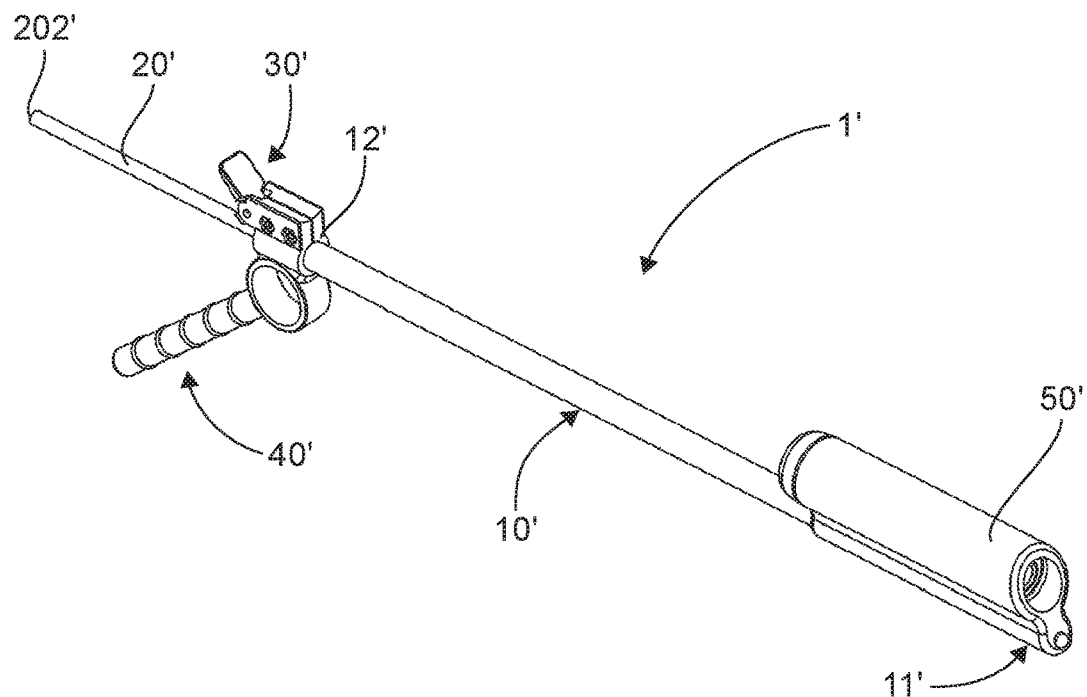
FIG. 10 is a perspective view of a device for the artificial insemination and vaginal and uterine observations and sample collection for livestock, according to a second specific embodiment of the invention.

FIG. 10 is a perspective view of a device for the artificial insemination, vaginal and cervical examination, and uterine treatment and sample collection for livestock, according to a second specific embodiment of the invention.

This second embodiment differs from the first in the structure of its guiding sleeve and the structure of its gripping assembly.

In this second embodiment, the device 1' comprises a guiding sleeve 10' formed of a hollow cylindrical tube as a single element, with a proximal end 11' designed for insertion into the vagina of the animal, and a distal end 12' designed to be operated by the user during an insemination procedure.

The insemination gun 20' is identical to that described in the first embodiment, and thus comprises a front end 201', intended to be positioned in the cervix of the animal, and a rear end 202', intended to be used by the operator to inject the contents of a semen straw into the uterus of the animal.

The device 1' for the artificial insemination of livestock comprises a locking means 30' to prevent sliding of the insemination gun 20' inside the guiding sleeve 10'.

In this second embodiment, the locking means 30' is broadly identical to that illustrated in FIG. 7.

In this sense, the locking means 30' located at the distal end 12' of the guiding sleeve 10' comprise a mobile pad 31' connected to a tab 32' which itself is mounted on a bracket 41' in a pivoting manner. The bracket 41' is affixed to a topside portion of the guiding sleeve 10'.

In this way, the user can pivot the tab 32 with a movement of the thumb so that the pad 31A exerts sufficient pressure on the insemination gun 20 to immobilise it.

Figure 11:
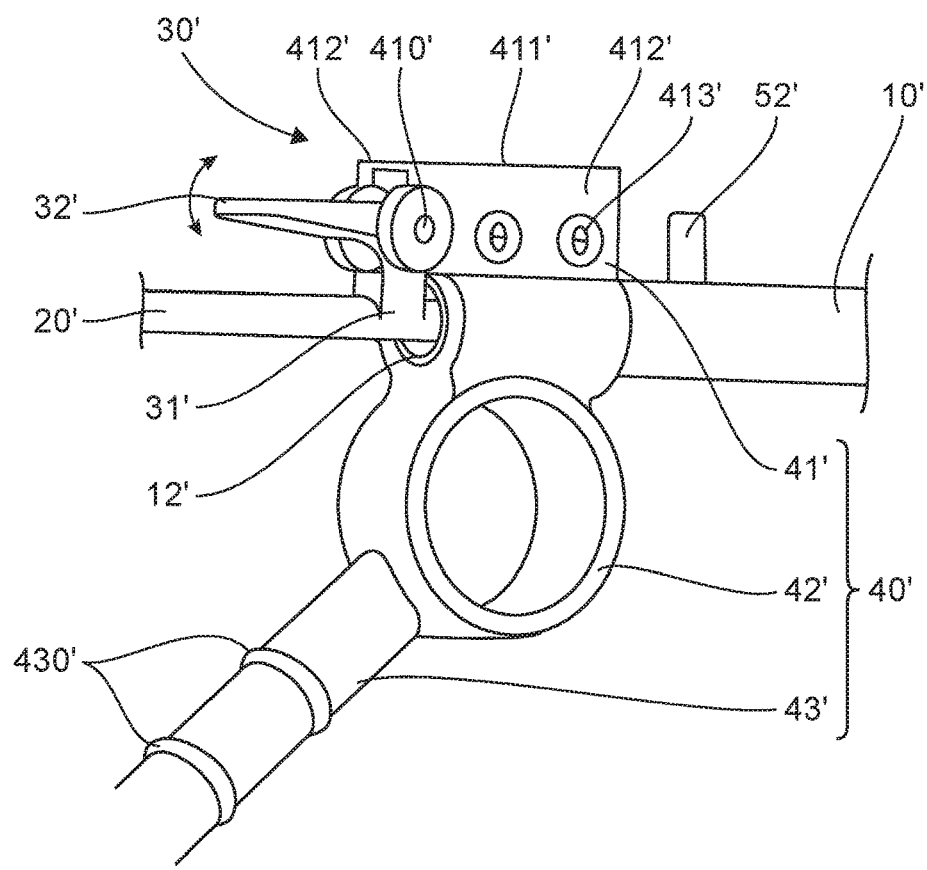
FIG. 11 is a detailed view of the distal end of the guiding sleeve of the device shown in FIG. 10.

In this second embodiment, the gripping assembly 40', shown in FIGS. 10 and 11, extends obliquely from the locking means 30' and is located at the distal end 12' of the guiding sleeve 10'.

The gripping assembly 40' comprises the bracket 41', a ring 42' located underneath the guiding sleeve 10', and a handle 43' extending obliquely from the ring 42'.

The guiding sleeve 10' is thus located between the bracket 41' and the ring 42'.

The bracket 41', with the tab 32' at its rear end, has a concave upper surface 411' where the operator may place his/her thumb when not using the tab 32' to activate the locking means 30'.

The ring 42' is designed to receive the index finger of one hand of the user, regardless of size or shape.

The handle 43', which takes the form of a rod, has ribs 430' to provide the user with a firm grip on the handle.

This ergonomic gripping assembly 40' allows the user to manipulate the insemination device 1 with ease, precision and stability, whether he/she is left-handed or right-handed.

In the example illustrated, the bracket 41' is composed of two half-shells 412, 412' joined together with fixing screws 413' around the guiding sleeve 10'.

This allows the gripping assembly 40' to be quickly and easily detached from the guiding sleeve 10' to minimise the space needed to store the device 1' when not in use and/or for easier cleaning, for example.

In this second embodiment, the guiding sleeve 10' does not comprise housing for a camera 50' that allows the user to see, on a remote monitor (not shown, the area of the reproductive tract of the animal where the proximal end of the guiding sleeve is currently located.

Figure 12:
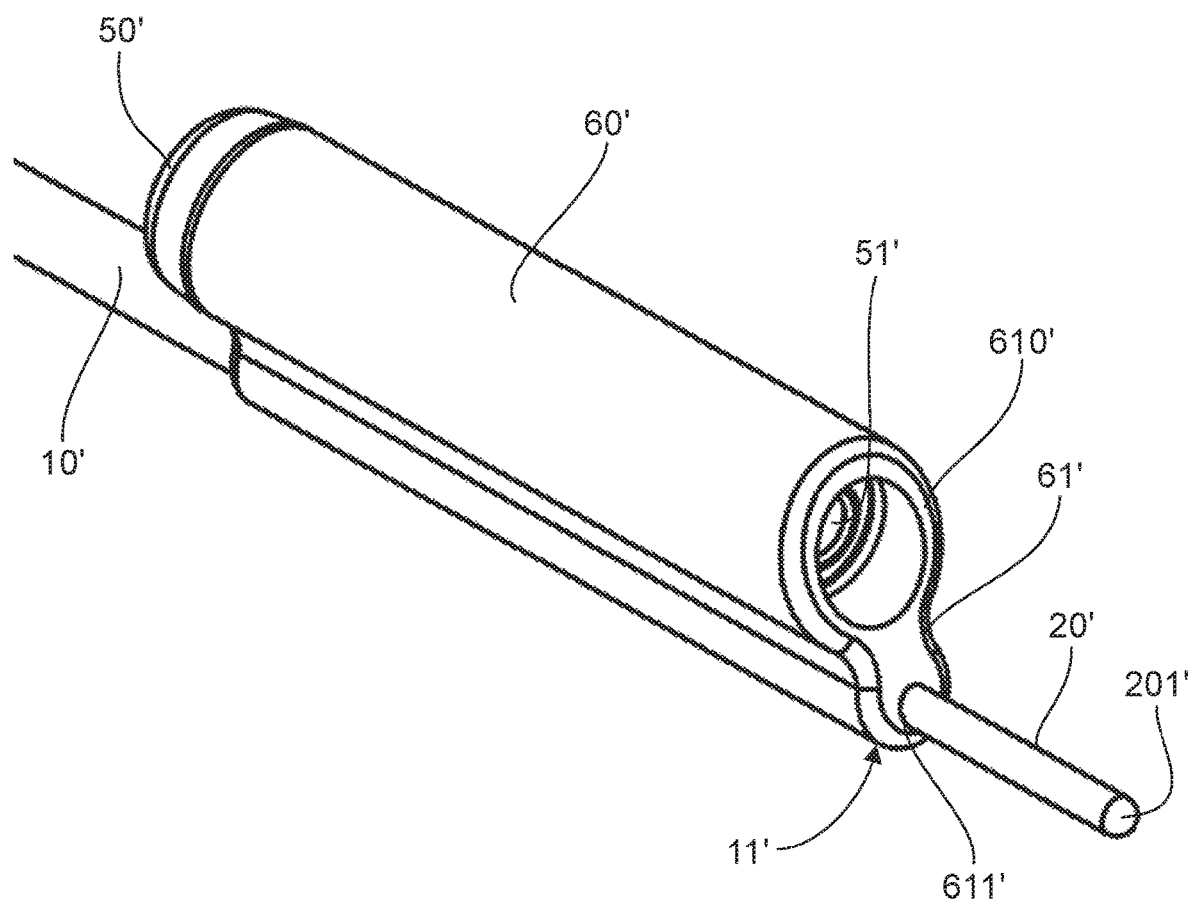
FIG. 12 is a detailed view of the proximal end of the guiding sleeve of the device shown in FIG. 10.

The camera 50', which can be seen in FIG. 12, and the proximal end 11' of the guiding sleeve 10' are surrounded by a protective sheath 60' that connects the two together.

The front end 61' of the protective sheath 60' has a smooth face inclined rearwards and rounded edges, to simplify penetration of the device 1' past the tight folds inside the reproductive tract of the animal.

This inclined face has an opening 610' for the camera lens 51', which is slightly recessed inside the camera.

This inclined face has another opening 611' located opposite an aperture at the proximal end 11' of the guiding sleeve 10', through which the front end 201' of the insemination gun 20' is able to pass (this front end 201' is shown extending beyond the proximal end 11' in FIG. 12).

The camera 50' is equipped with a system to transmit the captured images to a remote monitor.

In the embodiment illustrated, the transmission system is wireless and comprises an antenna with one end connected to the camera 50' and the other end, called the free end 52', protruding from the guiding sleeve 10' near the locking means 30', as shown in FIG. 11.

The free end 52' of the antenna is located, for example, approximately 4 mm from the bracket 41' for the gripping assembly 40' and between said gripping assembly and the camera 50'.

This specific location of the free end 52' of the antenna helps improve the transmission quality of the captured images sent to the remote monitor.

In the embodiment illustrated, the guiding sleeve 10' is made from an injection moulded plastic.

In one variant of this embodiment, the sleeve is made from stainless steel.

In the embodiment illustrated, the guiding sleeve 10' has a diameter between 5 and 10 mm, preferably 6 mm.

The small diameter of the guiding sleeve 10' grants greater freedom of movement when the sleeve is inside the reproductive tract of the animal, and also facilitates positioning of the front end of the insemination gun 20' so that it is aligned with the entry to the cervix of the animal.

In the embodiment illustrated, the camera 50' comprises light sources to illuminate the area of the reproductive system of the animal in front of the proximal end of the guiding sleeve 10'.

In the embodiment illustrated, the lens of the camera 50' is made from a material, such as glass, that prevents the occurrence of fogging.

In the embodiment illustrated, the camera 50' comprises an on/off switch located on its rear face.

The switch may be covered by a flexible and seal-tight protective membrane.

In the embodiment illustrated, the antenna extends into a groove inside the guiding sleeve 10'.

In a variant of this embodiment, the groove is formed of an additional channel that is attached to the inside of the guiding sleeve 10' by at least two hooks.

The first hook is located near the camera 50', and the second is located near the gripping assembly 40'.

In a variant of this embodiment, the groove is integrated into the guiding sleeve during manufacture.

In the embodiment illustrated, the free end 52' of the antenna is covered by a flexible, water-tight seal that can partially penetrate inside the guiding sleeve 10' or groove.

In a variant of this embodiment, the internal diameter of the guiding sleeve 10' can be reduced at its proximal end for improved guidance of the front end of the insemination gun 20'.

The proximal end 11' of the guiding sleeve 10' can be plugged with a stopper when the device 1' is being used for gynaecological observations, for example.

The invention claimed is:

1. A device for at least one of artificial insemination, gynaecological examination of a vagina and cervix, intrauterine treatments or uterine sample collection in livestock, the device comprising:
    a guiding sleeve with a proximal end to be positioned in a reproductive system of an animal and a distal end to be handled by a user; and a gynaecological instrument that slides within said guiding sleeve and that can be operated by the user at a rear end of said instrument, located beside the distal end of the guiding sleeve, so that a front end of said instrument passes through an opening located at the proximal end of said guiding sleeve for at least one of insemination, treatment or sample collection, wherein said guiding sleeve comprises a lock for blocking a sliding of the instrument inside said guiding sleeve so as to prevent any unintentional back movement of said instrument into the guiding sleeve, wherein said lock comprises at least one mobile pad that can be set to a locked position wherein said at least one mobile pad is in contact with the instrument and prevents the instrument from moving, and a retracted position wherein said at least one mobile pad is located at a distance from said instrument and permits a sliding movement of the instrument.

2. The device of claim 1, wherein said lock is located at the distal end of the guiding sleeve.

3. The device of claim 1, wherein said lock has a single friction pad capable of exerting a friction force against said instrument.

4. The device of claim 1, wherein said lock has at least two mobile pads arranged opposite and spaced apart from each other to exert a pinching force around said instrument.

5. The device of claim 1, wherein said lock comprises a pivoting tab for manual actuation of said lock.

6. The device of claim 1, wherein said guiding sleeve comprises a gripping assembly arranged near said lock.

7. The device of claim 6, wherein the gripping assembly comprises a ring located underneath the guiding sleeve, to receive an index finger of a hand of the user.

8. The device of claim 7, wherein the gripping assembly also comprises a concave surface on a top of the guiding sleeve, to receive a thumb of said hand of the user.

9. The device of claim 1, wherein the proximal end of said guiding sleeve comprises a camera.

10. The device of claim 9, wherein said camera is located inside of the guiding sleeve.

11. The device of claim 10, wherein said device comprises a transmitter to transmit images captured by said camera to a remote display screen, whereby said transmitter is located inside the distal end of said guiding sleeve.

12. The device of claim 1, wherein a diameter of said guiding sleeve is between 6 mm and 25 mm.

13. The device of claim 1, wherein said guiding sleeve comprises first and second parts that are secured together in a removable manner via complementary interlock.

14. The device of claim 13, wherein the complementary interlock comprises a seal at a junction between the first and second parts.

15. The device of claim 1, wherein the gynaecological instrument is an insemination gun, an insemination or treatment catheter, or a sampling swab.

16. A device for at least one of artificial insemination, gynaecological examination of a vagina and cervix, intra-uterine treatments or uterine sample collection in livestock, the device comprising:

a guiding sleeve with a proximal end to be positioned in a reproductive system of an animal and a distal end to be handled by a user; and a gynaecological instrument that slides within said guiding sleeve and that can be operated by the user at a rear end of said instrument, located beside the distal end of the guiding sleeve, so that a front end of said instrument passes through an opening located at the proximal end of said guiding sleeve for at least one of insemination, treatment or sample collection, wherein said guiding sleeve comprises a lock for blocking a sliding of the instrument inside said guiding sleeve so as to prevent any unintentional back movement of said instrument into the guiding sleeve, and wherein said guiding sleeve comprises a gripping assembly arranged near said lock, the gripping assembly comprising a ring located underneath the guiding sleeve, to receive an index finger of a hand of the user and a concave surface on a top of the guiding sleeve, to receive a thumb of said hand of the user.

* * * * *